United States Patent [19]

Gedeon

[11] Patent Number: 4,753,245
[45] Date of Patent: Jun. 28, 1988

[54] APPARATUS FOR MEASURING THE OXYGEN UPTAKE OF A PERSON

[75] Inventor: Andras Gedeon, Täby, Sweden

[73] Assignee: ICOR AB, Bromma, Sweden

[21] Appl. No.: 840,916

[22] Filed: Mar. 18, 1986

[30] Foreign Application Priority Data

Mar. 26, 1985 [SE] Sweden .............................. 85014918

[51] Int. Cl.$^4$ ............................................... A61B 5/08
[52] U.S. Cl. .................................... 128/718; 128/719; 128/205.15
[58] Field of Search .................. 128/718, 719, 205.14, 128/205.15

[56] References Cited

U.S. PATENT DOCUMENTS 2,592,694 4/1952 Heidbrink ........................... 128/2.07
4,231,362 11/1980 Pearson et al. .................. 128/205.15

OTHER PUBLICATIONS

Leach, Science, Mar. 15, 1946, vol. 103, No. 2672, pp. 341–342.

Primary Examiner—Kyle L. Howell
Assistant Examiner—John C. Hanley
Attorney, Agent, or Firm—Lahive & Cockfield

[57] ABSTRACT

Figure 1:
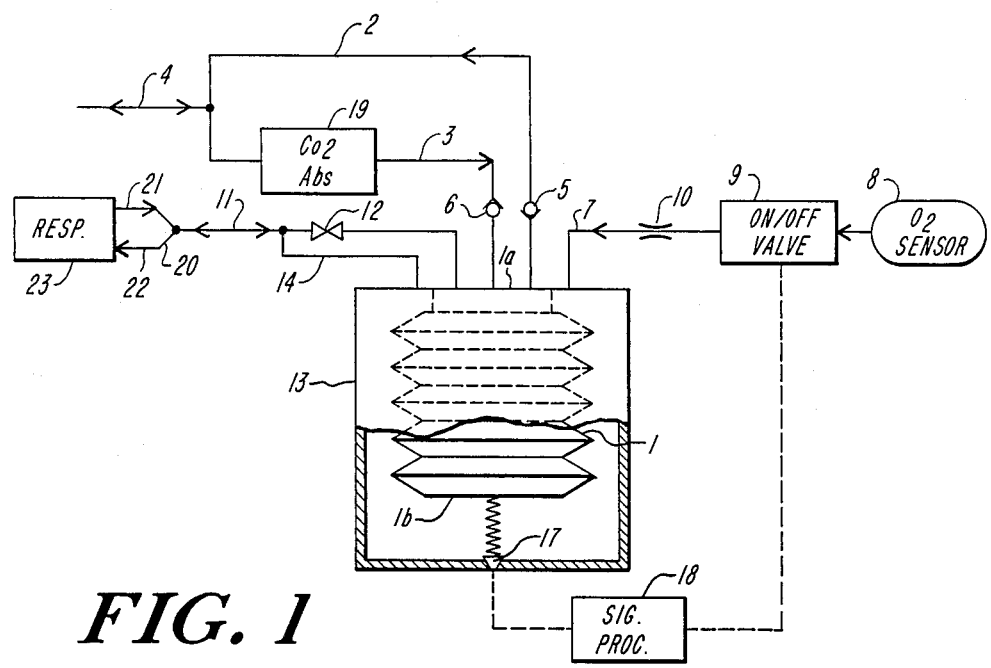

Apparatus for measuring the oxygen uptake of a person connected to a respirator (23) includes a closed container (1) of variable volume. The container (1) can be connected to the respiratory passages of the person, via an inspiration line (2) and an expiration line (3), so that the person can inspire from and expire to the container (1). One of the lines incorporates a carbon dioxide absorber (19) for removing carbon dioxide from the respiratory gas. Means (17,18) are provided for monitoring the volume of the container (1), and controllable means (8,9,10) are found for supplying pure oxygen gas to the container (1). The oxygen-gas supply means (8,9,10) are so controlled by the means (17,18) monitoring the volume of the bellows (1) that the volume of the bellows at a given predetermined point in the breathing cycle of the person connected to the apparatus is held substantially unchanged. Means are also provided for determining the amount of oxygen gas supplied to the container (1) herewith. The interior of the container (1) is connected to the respirator (23), via a line (11) incorporating closure means (12), so that prior to the actual measuring process the person connected to the apparatus obtains assistance in breathing from the respirator via the interior of the container (4) and the volume of gas therein assumes a state of equilibrium with respect to temperature and relative humidity prior to commencing the measuring operation. The variable container (1) is enclosed in an outer, rigid vessel (13), the interior of which communicates with the respirator (23), so as to provide requisite breathing assistance during the actual measuring process. (FIG. 1).

4 Claims, 1 Drawing Sheet

APPARATUS FOR MEASURING THE OXYGEN UPTAKE OF A PERSON

The present invention relates to apparatus intended for measuring the amount of oxygen absorbed by a person, i.e. the oxygen uptake.

The desirability of being able to measure the oxygen up-take of a person in a simple and reliable manner is to be found in many different medical contexts, and also in other connections, for example in the field of athletics and in industrial life. These measurements can be used, for example, to determine the effectiveness or efficiency of the respiratory system of both sick and healthy people, for example athletes, and also to determine the degree of strain created by a specific working situation. By converting into calories the amount of oxygen absorbed and combusted by the body, it is also possible to establish the amount of nutrient required by a person in order to prevent that person from starving or from being over-fed. It is desirable to be able to measure the amount of oxygen absorbed by a person in a reliable and simple manner, and also to be able to make such measurements irrespective of whether the person concerned breathes spontaneously from the ambient air or is connected to a respirator from which the person concerned is supplied with breathing gas more or less forcibly.

In principle, those apparatus which are used at present, or which have been previously proposed, to measure the amount of oxygen absorbed by a person fall in two different categories.

A first of these categories utilizes an open system, in which measurements are taken of the amount of oxygen supplied to and inspired by a person, and also of the amount of oxygen expired by said person. Such open systems require the provision of expensive measurement transdurcers effective to measure the magnitude of the gas flows and their respective oxygen contents, and also the provision of a complicated system for making those corrections necessary to achieve an acceptable degree of accuracy. Despite this, the open systems do not function satisfactorily when the inspired gas has an oxygen content in excess of about 50%.

The second category utilizes a closed system, in which a person inspires and expires from and to a closed volume of gas, which at the beginning of a measuring sequence contains 100% pure oxygen-gas, and in which the amount of oxygen absorbed is measured upon completion of the measuring sequence, by determining the change in the magnitude of the closed gas volume. Naturally, these known closed systems cannot be used to measure oxygen uptake continuously, and neither can they be used readily to measure the oxygen uptake of people who must be connected to a respirator or the like. Also known in the art is a variant of the closed system in which the closed gas-volume is filled with pure oxygen gas during a measuring sequence, so as to maintain the oxygen content of the gas at a constant average level. A system of this kind, however, has an extremely slow response, i.e. the measuring process is encumbered with an extremely large time constant, and also relies upon the use of sensitive tranducers to measure the oxygen-gas content of the closed-gas volume, and also upon the provision of expensive and complicated control devices for regulating the supply of gaseous oxygen to the closed gas-volume.

Finally, U.S. Pat. No. 2,592,694 describes and illustrates apparatus of the closed kind, which include a closed, variable-volume container in the form of bellows which are connected to the breathing passages of the person concerned, so that said person inspires from and expires into the container. Means are provided for removing carbon dioxide ($CO_2$) from the expiration gas. In addition, the apparatus also includes means for monitoring the volume of the variable container, together with means which are controlled by said monitoring means and which are effective in supplying pure oxygen gas to the container in quantities required to maintain a constant average container volume during inspiration and expiration of the person concerned, wherewith the amount of oxygen absorbed by the person can be determined by measuring the amount of oxygen supplied to the container. This known apparatus has a number of fundamental advantages, although the device for monitoring the volume of the variable container and for controlling the supply of oxygen gas thereto in response to said monitoring process are extremely complicated and highly sensitive to disturbances. The apparatus is also encumbered with a very serious drawback, insomuch that it cannot be used to measure the oxygen uptake of a person who is incapable of breathing spontaneously to a satisfactory degree without needing to be connected to a respirator, this drawback being shared by the other known apparatus aforementioned.

Consequently, an object of the present invention is to provide an apparatus which is simpler, more reliable, more accurate and more effective than the aforementioned apparatus of this kind, and which can be used to measure the oxygen uptake or absorbtion of a person whose condition makes it necessary to connect him/her to a respirator.

The characteristic features of the apparatus according to the invention are set forth in the following claims.

Figure 2:
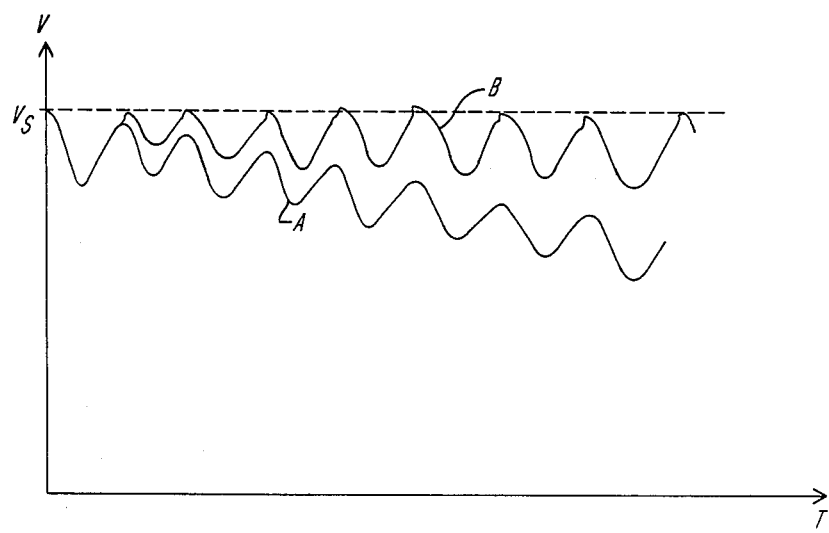

The invention will now be described in more detail with reference to the accompanying drawings, in which FIG. 1 illustrates schematically an advantageous exemplifying embodiment of the invention, and FIG. 2 is a diagram illustrating the manner of operation of the apparatus illustrated in FIG. 1.

The embodiment of the apparatus according to the invention illustrated by way of example in the drawings includes a container 1 of variable volume, which in this embodiment has the form of bellows having a first stationary end-wall 1a and a second end-wall 1b which is arranged to move in agreement with variations in the volume of the container 1. The container 1 is connected to an inspiration line 2 and an expiration line 3, which in turn are connected to a common line 4, which can be connected in a convenient, conventional manner (not shown) to the breathing passages of the person whose oxygen uptake is to be measured. The inspiration line 2 and the expiration line 3 have incorporated therein respective non-return valves 5 and 6, which are adapted to permit gas to flow solely in one direction, i.e. to the patient through the inspiration line 2 and away from the patient through the expiration line 3. The expiration line 3 also incorporates an absorption device 19 which is effective to remove carbon dioxide from the expiration gas expired by the patient through the line 3 and passing to the container 1. This $CO_2$-absorber 19 may be of any known type suitable for the purpose intended. The $CO_2$-absorber may be incorporated in the inspiration line 2, instead of the expiration line 3.

The interior of the container 1 communicates through a line 7 with an arrangement effective to control the supply of pure oxygen gas to the container 1.

This arrangement includes a suitable constant pressure oxygen-gas source 8, not shown in detail, which can be placed in communication with the line 7, and therewith the container 1, through a controllable on-off-valve 9 and a constriction 10.

The container 1 is also connected to a line 11 which incorporates a shut-off valve 12 which is connected, by a conventional, schematically illustrated Y-piece, to the inspiration and expiration lines 21 and 22 respectively of the respirator 23 used to provide respiratory assistance to the person connected to the line 4 and whose oxygen uptake is to be measured.

The variable volume container, or bellows, 1 is arranged in an outer, rigid vessel 13, the interior of which is connected to a line 14 which is connected in turn to the line 11 in a manner such as to be constantly connected to the inspiration and expiration lines 21,22 of the respirator 23.

Finally, the apparatus according to the invention also incorporates means for monitoring the volume of the container 1. In the case of the illustrated embodiment, monitoring of the container volume is effected by monitoring the position or movement of the moveable endwall 1b of the bellows 1, said wall moving in agreement with the variations in the volume of the container or bellows 1. In the case of the illustrated embodiment, this is effected with the aid of a suitable conventional ultrasonic distance meter 17, which has only been shown schematically and which transmits ultra-sonic signals onto the moveable wall 1b of the bellows 1 and receives the ultra-sonic signals reflected from said wall and measures, in a known manner, the distance from the moveable wall 1b to a stationary point. The ultra-sonic distance meter 17 controls the on-off-valve 9 in the oxygen-gas supply line 7, via suitable signal processing circuits 18, in a manner hereinafter described.

The apparatus has the following principle manner of operation, it being assumed here that the person connected to the line 4 is incapable of breathing satisfactorily herself/himself, and thus needs to be connected to a respirator in order to obtain assistance in breathing. To this end, the line 11 is connected to the respirator 23 used in the manner aforedescribed with reference to FIG. 1.

The valve 12 is kept closed during the actual measuring process, and hence the person connected to the apparatus inspires from the volume of gas present in the bellows 1 through the inspiration line 2, and expires into the bellows 1 through the expiration line 3, wherewith the carbon dioxide present in the respiratory air is removed by the $CO_2$-absorber 19. In this respect, the patient obtains the necessary breathing assistance due to the fact that the respective inspiration and expiration lines 21 and 22 of the respirator 23 communicate with the space located between the rigid, outer vessel 13 and the bellows 1, via the Y-piece 20, the line 11 and the line 14. During the inspiration phase of a breathing cycle controlled by the respirator 23, the respirator will therefore supply gas to the interior of the rigid vessel 13 at a suitable adapted pressure and in a suitably adapted amount, therewith pressing the bellows 1 together and causing the person connected to the line 4 to breathe in. In the subsequent expiration phase of the breathing cycle controlled by the respirator 23, the pressure is lowered in the rigid vessel 13 and the gas present therein is led out through the line 14, the line 11, the Y-piece 20 and expiration line 22 of the respirator 23, wherewith the bellows 1 are able to expand, to enable the person connected to the line 4 to exhale. Thus, despite not being connected directly to the respirator 23 during a measuring sequence, the person concerned still obtains the breathing assistance required from the respirator 23, but through the bellows 1. It will be understood that the volume of gas expired will be smaller than the volume of gas inspired, by an amount corresponding to the amount of oxygen absorbed and combusted by the person concerned. Thus, if no measures are taken to replace the oxygen gas consumed, the volume of the bellows 1, or if preferred the position of the moveable bellows-wall 1b, will in principle vary in the manner illustrated schematically by the curve A in the diagram presented in FIG. 2, this diagram illustrating the variations in the volume V of the bellows as a function of the time T, the initial volume of the bellows 1 being designated $V_S$. As illustrated by the curve A, under the circumstances assumed the volume of the bellows 1 should vary in keeping with the inhalations and exhalations performed by the person connected to the apparatus, and should also decrease gradually as a result of the oxygen absorbed by the person concerned.

According to the invention, however, the volume of the bellows 1 is monitored with the aid of the ultra-sonic distance meter 17 which detects the position taken by the moveable wall 1b of the bellows 1, the distance meter in turn influencing the valve 9 in the line 7, via the signal processing circuits 18, so that pure oxygen gas is supplied to the bellows 1 from the oxygen-gas source 8 in an amount corresponding to the amount of oxygen gas consumed by the oxygen uptake of the person concerned, so as to maintain, on average, the volume of the bellows 1 unchanged. With knowledge of the volume of oxygen gas supplied through the line 7, a measurement can be obtained of the oxygen uptake of the person connected to the apparatus.

In principle, this could be effected by designing the signal processing circuit 18 in a manner to determine the mean value of the bellows volume on the basis of the signal delivered by the ultra-sonic distance meter 17, this signal representing the position of the moveable wall 1b of the bellows 1 at that particular moment in time, and therewith also the momentary volume of the bellows 1, and to constantly maintain this mean volume by making necessary adjustments to the setting of the valve 9 in the oxygen-gas supply line 7. However, due to the wide variations occurring in the volume of the bellows 1 as a result of the inhalations and exhalations performed by the person connected to the apparatus, which inhalations and exhalations may have a highly varying and uneven frequency and also may be of varying magnitude, such a method is relatively complicated and inexact, and above all is encumbered with a significant time delay.

Consequently, it is proposed in accordance with the invention that the signal processing circuit 18 is constructed in a manner to establish on the basis of the signal from the ultra-sonic distant meter 17 the volume of the bellows 1 upon termination of each expiration phase of the breathing cycle of the person connected to the apparatus, i.e. the point at which the volume of the bellows 1 is at its maximum. The bellows volume at the end of each expiration phase is compared with the initial volume $V_S$ of the bellows stored in the signal processing circuit 18, and if the real volume of the bellows 1 at the end of an expiration phase falls beneath the initial volume $V_S$ by more than a given amount, the valve 9 is opened through the circuit 18 and is held open for a predetermined, suitably adapted period of time. Because the oxygen-gas source 8 is under constant pressure, and the oxygen gas is supplied to the bellows 1 through the open valve 9 and the aforementioned constriction 10, a predetermined amount of oxygen gas will be supplied to the bellows 1 each time the valve is opened in this way by the signal processing circuit 18. Thus, upon completion of the exhalation phases of the person connected to the apparatus, the volume of the bellows 1 will thus be maintained substantially unchanged and in accord with the initial volume $V_S$ of the bellows, in addition to which it is possible to readily measure the amount of oxygen gas supplied to the bellows 1 to this end, by counting the number of times the valve 9 has been opened by the signal processing circuit 18.

It will be understood that the signal processing circuit 18 could be constructed to establish, on the basis of the signal from the distance meter 17, the volume of the bellows 1 at some other given point in the breathing cycle of the person connected to the apparatus, although it has been found that from a practical aspect the point at which expiration terminates constitutes a well defined and readily detected point for determining the volume of the bellows 1. Thus, in the case of the illustrated preferred embodiment of the apparatus according to the invention, the volume of the bellows 1 will, in principle, vary during a measuring sequence in the manner illustrated by the curve B in FIG. 2.

A value representative of the volume taken by an adult person with each breath is about 500 ml, wherewith the oxygen uptake, and therewith the difference between the inspired gas volume and the expired gas volume, may be about 20 ml. The bellows 1 of the apparatus according to the invention may, for example, thus have a volume of about 3 l. It will be understood that in order to measure accurately, it is essential that the volume of gas present in the bellows 1 has a constant temperature and constant relative humidity during the whole of the measuring sequence. This is achieved in accordance with the invention by holding the valve 12 open before the start of the actual measuring process, wherewith the person connected to the line 4 breathes from and to the respirator 23 through the bellows 1, the valve 12 and the line 11 connected to the respirator. This is allowed to continue until the volume of gas within the bellows 1 substantially assumes a state of equilibrium with regard to temperature and relative humidity. The valve 12 is then closed and the measuring process carried out in the aforedescribed manner.

It will be understood that apparatus according to the invention can also be used to measure the oxygen uptake of a person capable of breathing spontaneously, and consequently not needing assistance from a respirator. In cases such as these the line 11 is not connected to a respirator, but is instead left in open communication with the ambient air. The measuring process is effected in other respects in the same manner as that described above.

It will also be understood from the aforegoing that the invention is not restricted to the described and illustrated exemplifying embodiment, and that modifications can be made to the illustrated apparatus and that other embodiments of apparatus according to the invention can be envisaged. For example, the container 1 of variable volume may have various different forms, as can also the arrangement for monitoring the volume of the container and the means controlled by said arrangement for supplying oxygen gas to the container and for measuring the amount of oxygen gas supplied.

I claim:

1. An apparatus for measuring the oxygen uptake of a person comprising a respirator, having an inhalation line and an exhalation line;

a closed container of variable volume;

connecting means for connecting the container to the respiratory passages of said person, so that the person is able to inhale from and exhale to the container;

means incorporated in said connecting lines for removing carbon dioxide;

means for monitoring the volume of the container;

oxygen-gas supply means responsive to said volume monitoring means and connected to the container for supplying pure oxygen gas thereto in such an amount controlled by said volume monitoring means that the volume of the container remains substantially constant at a given point in each breathing cycle of the person;

means for determining the amount of oxygen gas supplied to the container;

connecting means for connecting the interior of the container to both the inhalation line and the exhalation line of the respirator, said connecting means being provided with shut-off means for selectively opening and interrupting, respectively, the connection between the interior of the container and the inhalation and exhalation lines of the respirator;

an outer rigid vessel, surrounding the container, having a fixed volume; and connecting means for connecting the interior of said rigid vessel permanently to both the inhalation line and the exhalation line of the respirator between the respirator and the shutoff valve.

2. An apparatus as claimed in claim 1, wherein said container has the form of bellows having a stationary end-wall and a moveable end-wall which moves in response to variations in volume of the container; and said volume monitoring means include means for monitoring the position taken by the moveable bellows-wall by transmitting ultra-sonic signals from a stationary point onto the moveable bellows-wall and receiving ultra-sonic signals reflected from the moveable bellows-wall.

3. An apparatus as claimed in claim 1, wherein said oxygen-gas supply means include an oxygen-gas source of constant pressure connected to the interior of the variable container via a constriction and a controllable valve, said valve being so controlled by said volume monitoring means as to be opened and held open for a given length of time each time the volume of the container at said point in the breathing cycle of said person falls beneath a given value; and said means for determining the amount of oxygen gas supplied include means for counting the number of times said valve has been opened.

4. An apparatus as claimed in claim 1, wherein said given point in each breathing cycle is upon completion of the expiration phase in each breathing cycle.

* * * * *